United States Patent
Barron et al.

(10) Patent No.: US 6,440,947 B1
(45) Date of Patent: *Aug. 27, 2002

(54) METHOD FOR TREATING OCCLUSIVE PERIPHERAL VASCULAR DISEASE AND CORONARY DISEASE

(75) Inventors: Hal V. Barron, San Francisco; Elias Botvinick, San Rafael, both of CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/167,816

(22) Filed: Oct. 7, 1998

Related U.S. Application Data

(63) Continuation-in-part of application No. 08/946,196, filed on Oct. 7, 1997.

(51) Int. Cl.$^7$ .......................... A61K 31/70; A01N 43/04
(52) U.S. Cl. ............................ 514/46; 514/46; 514/56; 514/59; 514/62
(58) Field of Search .................... 514/46, 56, 59, 514/62

(56) References Cited

U.S. PATENT DOCUMENTS

| | | |
|---|---|---|
| 3,819,612 A | 6/1974 | Imai et al. |
| 3,819,613 A | 6/1974 | Marumoto et al. |
| 4,738,954 A | 4/1988 | Hamilton et al. ............. 514/46 |
| 4,868,160 A | 9/1989 | Hamilton et al. ............. 514/46 |
| 4,886,786 A | 12/1989 | Lindstrom et al. |
| 4,954,504 A | 9/1990 | Chen et al. |
| 5,034,381 A | 7/1991 | Hutchison et al. |
| 5,063,233 A | 11/1991 | Chen et al. |
| 5,104,859 A | 4/1992 | Sollevi |
| 5,140,015 A | 8/1992 | Olsson et al. |
| 5,206,222 A * | 4/1993 | Forman et al. ................ 514/46 |
| 5,231,086 A | 7/1993 | Sollevi |
| 5,236,908 A | 8/1993 | Gruber et al. |
| 5,278,150 A | 1/1994 | Olsson et al. |
| 5,449,665 A | 9/1995 | Sollevi |
| 5,529,986 A | 6/1996 | Larsson et al. |
| 5,534,504 A | 7/1996 | Sollevi |
| 5,593,688 A | 1/1997 | Baldeschwieier |
| 5,593,875 A | 1/1997 | Wurm et al. |
| 5,731,296 A | 3/1998 | Sollevi |

FOREIGN PATENT DOCUMENTS

| | | |
|---|---|---|
| WO | 92/05177 | 4/1992 |
| WO | 96 12496 | 5/1996 |
| WO | 96 13158 | 5/1996 |
| WO | 96 18293 | 6/1996 |

OTHER PUBLICATIONS

Ofosu et al., Heparin and Related Polysaccharides, p. 3, 1989.*
Collins, Carbohydrates, p. 266, 1987.*
Japanese Abstract: JP01 187083 Nippon Mining Co. LTD, Jul. 1989.
Bautovich, G., et a., "Detection of Deep Venous Thrombi and Pulmonary Embolus with Technetium–99m–DD–3B6/22 Anti–fibrin Monoclonal Antibody Fab' Fragment," J. Nucl. Med. vol. 35, pp. 195–202 (1994).
Buckley and Sorkin, "Enoxaparin: A review of its pharmacology and clinical applications in the prevention and treatment of thromboembolic disorders," Drugs, vol. 44, pp. 465–497 (1992).
Chan, Sammy Y., "Comparison of Maximal Myocardial Blood Flow During Adenosine Infusion With That of Intravenous Dipyridamole in Normal Men," JACC, vol. 20, No. 4, pp. 979–985 (1992).
Chiarugi, V., "Cooperation of Heparin With Other Angiogenetic Effectors," International Journal of Tissue Reactions, VII(2), pp. 129–133 (1986).
Faulds, Diana, "Adenosine An Evaluation of its Use in Cardiac Diagnostic Procedures, and in the Treatment of Paroxysmal Supraventricular Tachycardia," Drugs, pp. 596–624 (1991).
Hara, Toshihiko, "Quantitative measurement of regional myocardial blood flow in patients with coronary artery disease by intravenous injection of $^{13}$N–ammonia in positron emission tomography," Nuclear Medicine, pp. 231–235 (1990).
Hutchins, Gary D., "Positron Emission Tomography to Quantitate Myocardial Perfusion," American Journal of Cardiac Imaging, vol. 7, No. 4, pp. 283–293 (1993).
Hutchins, Gary D., "Noninvasive Quantification of Regional Blood Flow in the Human Heart Using N–13 Ammonia and Dynamic Positron Emission Tomographic Imaging," JACC, vol. 15, No. 5, pp. 1032–1042 (1990).
Luria, Myron H., "Cardiovascular Risk Factor Clustering and Ratio of Total Cholesterol to High–Density Lipoprotein Cholesterol in Angiographically Documented Coronary Artery Disease," American Journal of Cardiology, vol. 67, pp. 31–36 (1991).
McAuslan, B.R., "Angiogenic Factors and Their Assay: Activity of Formyl Methionyl Leucyl Phenylalanine, Adenosine Diphosphate, Heparin, Copper, and Bovine Endothelium Stimulating Factor," Microvascular Research, pp. 323–338 (1983).

(List continued on next page.)

Primary Examiner—Johann Richter
Assistant Examiner—Howard Owens
(74) Attorney, Agent, or Firm—Burns, Doane, Swecker & Mathis LLP

(57) ABSTRACT

Compositions and methods for treatment of occlusive peripheral vascular disease and coronary disease are disclosed. The compositions and methods allow treatment of diseases associated with occlusion of coronary vessels, for example, by promoting growth of new blood vessels, i.e., angiogenesis and/or by recruitment of collaterals. The methods involve the co-administration of an adenosine $A_2$ receptor agonist, e.g., adenosine, and heparin and/or a heparin-like substance over a period of several days. In particular, this invention is applicable to improving collateral coronary circulation in patients suffering from myocardial infarction.

16 Claims, No Drawings

OTHER PUBLICATIONS

Schelbert, M.D., Heinrich R., "Consideration of Measurements of Myocardial Blood Flow with Positron–Emission Tomography," *Investigative Radiology*, vol. 28, Supp. 4, pp. S47–S55 (1993).

Soufer, M.D., Robert, et al., "Positron Emission Tomography And the Quantitative Assessment of Regional Myocardial Blood Flow," *JACC*, vol. 15, No. 1, pp. 128–130 (1990).

Symons, J. David, "Repeated Dipyridamole Administration Enhances Collateral–Dependent Flow and Regional Function During Exercise," *Department of Internal Medicine*, pp. 503–513 (1992).

Terrell, Grace E., "Indirect Angiogenic Agents Do Not Release Fibroblast Growth Factors From Extracellular Matrix," *Matrix*, vol. 11, pp. 108–114 (1991).

Tucker, K.J., "The applications of adenosine in noninvasive cardiac imaging," *Herz* 17, pp. 122–136 (1992).

Unger, Ellis F., "Heparin promotes the formation of extracardiac to coronary anastomoses in a canine model," *American Journal of Physiology*, vol. 260, No. 5, pp. H1625–H1634 (1991).

Valk, P.E., "Quantitative Assessment of Reversible Myocardial Ischemia by Dipyridamole Perfusion," *The Journal of Nuclear Medicine*, vol. 30, No. 5, pp. 760 (1989).

Araie, E. et al., "Heparin exercise treatment following percutaneous transluminal coronary angioplasty in a patient with effort angina," *Heart and Vessels*, vol. 6, pp. 181–183 (1991).

Ely, S.W. et al., "Protective effects of adensoine in myocardial ischemia," *Circulation*, vol. 85, No. 3, pp. 893–904 (1992).

Ethier, M.F. et al., "Adenosine stimulates proliferation of human endothelial cells in culture," *Am. J. Physiol.*, pp. H131–H138, (1993).

Fujita, M. et al., "Longterm efficacy of heparin exercise treatment for patients with chronic effort angina; evaluation by exercise T1–201 myocardial scintigraphy," *Int. J. Cardiol.*, vol. 40, pp. 51–56, (1993).

Fujita, M. et a., "Comparative effect of heparin treatment with and without strenuous exercise on treadmill capacity in patients with stable effort angina," *Am. Heart Journal.*, vol. 122, pp. 453–457, (1991).

Melandri, G. et al., "Benefit of adding low molecular weight heparin to the conventional treatment of stable angina pectoris. A double–bloind, randomized,placebo–controlled trial," *Circulation*, vol. 88, pp. 2517–2523, (1993).

Norrby, K. et al., "Heparin enhances angiogenesis by a systemic mode of action," *Int. J. Exp. Pathol.* vol. 73, pp. 147–155, (1992).

Sasayama, S. et al., "Recent insights into coronary collateral circulation," *Circulation*, vol. 85, pp.1197–1204, (1992).

Quyyumi, A. A. et al., "Angiogenic effects of low molecular weight heparin in patients with stable coronary artery disease: a pilot study." *J. Am. Coll. Cardiol.*, vol. 22, No. 3, pp. 635–641, (1992).

McAuslan, B. R., et al., "Angiogenic Factors and Their Assay: Activity of Formyl Methionyl Leucyl Phenylalanine, Adenosine Diphospharte, Heparin, Cooper, and Bovine Endothelium Stimulating Factor", *Microvascular Research*, vol. 26, No. 3, pp. 323–338, 1983.

Lutty, G. A., et al., "Adenosine Stimulates canine retinal microvascular endothelial cell migration and tube formation", *Current Eye Research*, 17 (6): 593–607, 1998.

* cited by examiner

METHOD FOR TREATING OCCLUSIVE PERIPHERAL VASCULAR DISEASE AND CORONARY DISEASE

CROSS REFERENCE TO RELATED APPLICATION

This application is a Continuation-in-part of a U.S. patent application Ser. No. 08/946,196, entitled "A METHOD FOR PROMOTING ANGIOGENESIS", filed Oct. 7, 1997, in the names of Hal V. Barron and Elias Botvinick.

FIELD OF THE INVENTION

The present invention relates to compositions and methods for treatment of occlusive peripheral vascular disease and coronary diseases, in particular, the occlusion of coronary vessels. More particularly, the invention relates to the promotion of the growth of new blood vessels (angiogenesis), especially coronary blood vessels, and/or the recruitment of collateral blood vessels, after myocardial infarction.

BACKGROUND OF THE INVENTION

It is estimated that five million people are afflicted with chronic stable angina in the United States. Each year 200,000 people under the age of 65 die with what is termed "premature ischemic heart disease." Despite medical therapy, many go on to suffer myocardial infarction and debilitating symptoms prompting the need for revascularization with either percutaneous transluminal coronary angioplasty or coronary artery bypass surgery. Medical researchers have postulated that one way of relieving myocardial ischemia would be to enhance coronary collateral circulation.

Fujita et. al. (Fujita et al., *Am. Heart Journal.*, 122:453 (1991), Fujita et al., *Int. J. Cardiol.*, 40:51 (1993)) demonstrated that heparin in combination with short term exercise training improved exercise tolerance as measured by dynamic exercise testing. The researchers, believing this effect was mediated through increased collateral vascular development, examined the effects of heparin in combination with a brief concomitant exercise training protocol on coronary collateral flow. Thallium-201 myocardial perfusion images obtained in association with the same work-load both before and late after combined heparin exercise treatment, which indicated that coronary collateral circulation was enhanced. Such dramatic changes over a short term do not occur naturally, and suggest that angiogenesis has taken place. These investigators carried out further studies which demonstrated that exercise alone or heparin alone were insufficient stimuli for collateral development (Fujita et al., *Am. Heart Journal*, 122:453 (1991)). That is, only when exercise and heparin were combined were they able to elicit this apparent angiogenic response. Other studies have suggested that exercise-induced ischemia combined with heparin increases coronary collateral flow.

More recently Quyyumi et. al. (Quyyumi et al., *J. Am. Coll. Cardiol.*, 22:635 (1993)) studied the anti-ischemic effects of combined treatment with low molecular weight heparin and exercise-induced ischemia. Twenty three patients received either heparin or placebo in combination with an exercise protocol for 4 weeks. Eighty percent of the low molecular weight heparin (LMWH) group compared with 31% of placebo group had a significant increase in rate-pressure product at the onset of 1 mm of ST segment depression. Further, the time to ischemia increased in 100% of the LMWH group compared with 62% in the placebo group. In this same population, the incidence and duration of ST segment depression, measured using an ambulatory holter monitor, decreased by 30 and 35% respectively compared with 0% in controls.

These authors concluded that exercise and LMWH lessens myocardial ischemia and that the improvement is likely to be mediated by enhanced collateral function. Similar findings resulted from another double-blind, randomized, placebo-controlled trial, involving 29 patients with stable exercise-induced angina pectoris who received a single daily subcutaneous injection of LMWH Pamaparin (trademark for a brand of heparin)

Correlations have now been made between the anatomic appearance of coronary collateral vessels ("collaterals") visualized at the time of intracoronary thrombolitic therapy during the acute phase of myocardial infarction and the creatine kinase time-activity curve, infarct size, and aneurysm formation. These studies demonstrate a protective role of collaterals in hearts with coronary obstructive disease, showing smaller infarcts, less aneurysm formation, and improved ventricular function compared with patients in whom collaterals were not visualized.

When the cardiac myocyte is rendered ischemic, collaterals develop actively by growth with DNA replication and mitosis of endothelial and smooth muscle cells. One hypothesis suggests that heparin-binding growth factors are present in the heart, or that biological activity is quiescent under normal physiological conditions. Once ischemia develops, these factors are activated and become available for receptor occupation, which may initiate angiogenesis after exposure to exogenous heparin. Unfortunately, the "natural" process by which angiogenesis occurs is inadequate to reverse the ischemia in almost all patients with coronary artery disease.

The etiology of the benefit of combined heparin-exercise treatment is unknown with certainty (Norrby and Sorbo, *Int. J. Exp. Pathol.* 73: 147 (1992), Sasayama and Fujita, *Circulation*, 85: 1197 (1992)). One possibility is that ischemia stimulates the release or expression of some angiogenic substance which in combination with heparin stimulates collateral development. However, a definitive link between an angiogenic substance and heparin to promote angiogenesis has not been established.

During ischemia, adenosine is released through the breakdown of ATP. Adenosine participates in many cardioprotective biological events. Adenosine has a role in hemodynamic changes such as bradycardia and vasodilation, and adenosine has been suggested to have a role in such unrelated phenomena as preconditioning and possibly the reduction in reperfusion injury (Ely and Beme, *Circulation*, 85: 893 (1992)).

Intrinsic adenosine may facilitate the coronary flow response to increased myocardial oxygen demands and so modulate the coronary flow reserve. Ethier et. al. (Ethier et al., *Am. J. Physiol.*, H131 (1993)) demonstrated that the addition of physiological concentrations of adenosine to human umbilical vein endothelial cell cultures stimulates proliferation, possibly via a surface receptor. They suggested that adenosine may be a factor for human endothelial cell growth and possibly angiogenesis. Angiogenesis appears to be protective for patients with CAD, but the rate at which blood vessels grow naturally is inadequate to reverse the disease. Thus, strategies to enhance and accelerate the body's natural angiogenesis potential should be beneficial in patients with CAD.

Combinations of thrombolytic agents such as streptokinase, urokinase and tissue plasminogen activator with adenosine have been proposed for use in providing coronary thrombolysis (see, for example, U.S. Pat. No. 5,534,504 to Sollevi). Sollevi does not teach that these agents, in combination with adenosine, provided any angiogenic benefit. Sollevi further teaches that administration of heparin is unsafe, and instead teaches administering adenosine in lieu of heparin.

There remains a need for an effective therapy for promotion of coronary angiogenesis with minimum side effects. Such a therapy would be particularly useful for patients who have myocardial infarctions and could be used prophylactically in patients who have poor coronary circulation which places them at high risk of ischemia and myocardial infarctions.

SUMMARY OF THE INVENTION

Compositions and methods for treatment of occlusive peripheral vascular disease and coronary diseases, in particular, the occlusion of coronary vessels, and disorders associated with the occlusion of the peripheral vasculature and/or coronary blood vessels, are disclosed. Also disclosed are compositions and methods for promoting angiogenesis and/or recruiting collateral blood vessels in a patient in need thereof. The compositions include an effective amount of heparin or a heparin-like substance and an effective amount of an adenosine $A_2$ receptor agonist. The compositions can be in the form of a sterile, injectable, pharmaceutical formulation that includes an angiogenically effective amount of heparin or a heparin-like substance and an adenosine $A_2$ receptor agonist in a physiologically and pharmaceutically acceptable carrier, optionally with one or more excipients.

The methods involve the co-administration of an effective amount of heparin or a heparin-like substance and an effective amount of an adenosine $A_2$ receptor agonist in low, daily dosages for a week or more. One or both components can be delivered locally via catheter. Heparin (or heparin-like substances) and relatively stable adenosine $A_2$ agonists (i.e., those with a half-life greater than about 15 minutes in vivo can be delivered to capillary beds surrounding ischemic tissue by incorporation of the compounds in an appropriately sized liposome or microparticle. Heparin can be targeted to ischemic tissue by covalent linkage with a suitable antibody.

The method may be used as a treatment to restore cardiac function after a myocardial infarction. The method may also be used to improve blood flow in patients with coronary artery disease suffering from myocardial ischemia or inadequate blood flow to areas other than the heart, for example, occlusive peripheral vascular disease (also known as peripheral arterial occlusive disease), where decreased blood flow is a problem.

DETAILED DESCRIPTION OF THE INVENTION

Compositions and methods for treatment of occlusive peripheral vascular disease and coronary diseases, in particular, the occlusion of coronary vessels, and disorders associated with the occlusion of the peripheral vasculature and/or coronary blood vessels, are disclosed. Also disclosed are compositions and methods for promoting angiogenesis and/or recruiting collateral blood vessels in a patient in need thereof. The compositions include an effective amount of heparin or a heparin-like substance and an effective amount of an adenosine $A_2$ receptor agonist. The methods involve the co-administration of an effective amount of heparin or a heparin-like substance and an effective amount of an adenosine $A_2$ receptor agonist in low, daily dosages for a week or more.

Definitions

As used herein, the term "myocardial ischemia" is defined as an insufficient blood supply to the heart muscle caused by a decreased capacity of the heart vessels.

As used herein, the term "coronary disease" is defined as diseases/disorders of cardiac function due to an imbalance between myocardial function and the capacity of coronary vessels to supply sufficient blood flow for normal function. Specific coronary diseases/disorders associated with coronary disease which can be treated with the compositions and methods described herein include myocardial ischemia, angina pectoris, coronary aneurysm, coronary thrombosis, coronary vasospasm, coronary artery disease, coronary heart disease, coronary occlusion and coronary stenosis.

As used herein the term "occlusive peripheral vascular disease" (also known as peripheral arterial occlusive disorder) is a vascular disorder involving blockage in the carotid or femoral arteries, including the iliac artery. Blockage in the femoral arteries causes pain and restricted movement. A specific disorder associated with occlusive peripheral vascular disease is diabetic foot, which affects diabetic patients, often resulting in amputation of the foot.

As used herein the terms "regeneration of blood vessels," "angiogenesis," "revascularization," and "increased collateral circulation" (or words to that effect) are considered as synonymous. The term "pharmaceutically acceptable" when referring to a natural or synthetic substance means that the substance has an acceptable toxic effect in view of its much greater beneficial effect, while the related the term, "physiologically acceptable," means the substance has relatively low toxicity. The term, "co-administered" means two or more drugs are given to a patient at approximately the same time or in close sequence so that their effects run approximately concurrently or substantially overlap. This term includes sequential as well as simultaneous drug administration.

As used herein, the term "heparin-like substance" refers to compounds which mimic the action of heparin. These include heparin-like glycosaminoglycans such as chondroitin sulfates; dermatan sulfates; heparan sulfates; low molecular mass heparin fragments such as ardeparin sodium, de-N-sulfated heparin, nitrous-acid deaminated heparin, and periodate-oxidized heparin; heparin fractions, and heparin salts such as ammonium, calcium, lithium, sodium, and zinc. The heparin-like substances preferably provide an anti-Xa Activity and anti-$II_a$ activity similar to that of heparin.

Other conventional anti-coagulants such as hirudin, ancrod, warfarin, tissue plasminogen factor, streptokinase, urokinase and Integrilin™ (commercially available from Cor Therapeutics), and combinations thereof are not intended to be equivalents of heparin, because they may exert their anti-coagulative effects by an entirely different mechanism. However, these can be present as optional components.

As used herein, a compound is an agonist of an adenosine $A_2$ receptor if it is able to fully inhibit adenylate cyclase and is able to displace $[^{125}I]$-AB-MECA in a competitive binding assay. The agonist can be effective toward the $A_{2a}$ or the $A_{2b}$ receptor.

A selective $A_2$ receptor agonist is one which has a ratio of $A_2/A_1$ activity greater than 50 and a ratio of $A_2/A_3$ activity greater than 50.

"Pharmaceutically acceptable salts" refers to pharmaceutically acceptable salts of heparin, a heparin-like substance, or an adenosine $A_2$ receptor agonist, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like can be used as the pharmaceutically acceptable salt.

I. Heparin and Heparin-Like Substances

A. Heparin

Heparin is a heterogeneous mixture of polysaccharides derived from beef or pork livers. Although the exact mechanism for heparin's antithrombotic properties is not known, it is believed to act by binding to antithrombin III. The heparin-antithrombin III complex inhibits the activity of numerous enzymes in the clotting cascade, including factors $II_a$ (thrombin), $IX_a$, $X_a$, $XI_a$, and $XII_a$ (Carter et al. "Enoxaparin: The low-molecular-weight heparin for prevention of postoperative thromboembolic complications," *Ann. Pharmacother.*, 27:1223–30 (1993); Olin, ed. Drug Facts and Comparisons. St. Louis: Facts and Comparisons, Inc., 1997:86b-g; Fareed and Hoppensteadt, "Pharmacology of the low-molecular-weight heparins," *Semin. Thromb. Hemostasis.* 22(Suppl 2):13–8 (1996); Fareed et al. "Are the available low-molecular-weight heparin preparations the same?" *Semin. Thromb. Hemostasis*, 22(Suppl 1):77–91 (1996); and Buckley and Sorkin, "Enoxaparin: A review of its pharmacology and clinical applications in the prevention and treatment of thromboembolic disorders," *Drugs*, 44:465–97 (1992)). In addition, heparin induces release of other endogenous antithrombotic substances, such as tissue factor pathway inhibitor and tissue plasminogen activator.

The effective dose of heparin can vary widely from patient to patient. A small percentage of patients who are administered heparin over an extended period of time develop heparin-induced thrombocytopenia (HIT). For this reason, it may be advantageous, at least for certain patients, to administer heparin-like substances instead of heparin. Suitable heparin-like substances are disclosed in detail below.

B. Chondroitin Sulfates

Chondroitin sulfates are structurally complex, sulfated, linear polysaccharides known as galactosaminoglycans (GAGS) comprising alternating uronic acid and N-acetyl-D-galactosamine residues. Chondroitin sulfates are localized on cell surfaces and in the extracellular matrix, and are important in cell to cell communications. They are the predominant GAGS comprising the proteoglycans produced by monocyte/macrophages.

Chondroitin Sulfate A (CSA) includes unsulfated glucuronic acid 1→3 linked to 4-O-sulfated N-acetyl-D-galactosamine which in turn is attached to the next glucuronic acid by a 1→4 linkage. Chondroitin Sulfate B, also known as Dermatan Sulfate or beta-heparin, is similar to CSA except that it contains iduronic acid instead of glucuronic acid. Chondroitin Sulfate C (CSC) has a 6-O-sulfate group and Chondroitin Sulfate E has a 4,6-di-O-sulfate on N-acetyl-D-galactosamine, in place of a 4-O-sulfate found in CSA. Suitable chondroitin sulfates include those described in Bjornsson et al., "The Anticoagulant Effect of Chondroitin-4-Sulfate, *Thromb Res.*, 27: 15–21 (1982); U.S. Pat. No. 3,895,106 to Morrison, Mazieres et al., "Chondroitin sulfate in the treatment of gonarthrosis and coxarthrosis," *Rev. Rhum. Mal. Osteoartic.*, 59: 466–72 (1992); and Nadkarni et al., "Preparation and biological activity of N-sulfonated chondroitin and dermatan sulfate derivatives," *Carbohydrate Res.*, 290:87–96 (1996), the contents of which are hereby incorporated by reference.

C. Dermatan Sulfates

Dermatan sulfate, also known as ββ-heparin or chondroitin sulfate B, is a polysaccharide composed of repeating uronic acid →N-acetyl-D-galactosamine disaccharides joined by 1,3 and 1,4 linkages. It is initially formed as a polymer composed of repeating glucuronosyl→galactosyl→galactosyl→xylosyl linkage regions. In its biosynthesis, some of the D-glucuronic acid residues are epimerized at C-5, converting them to L-iduronic acid residues, which is then followed by O-sulfation primarily at C-4, but also at C-6. Dermatan sulfate functions as an anticoagulant by catalyzing the inhibition of thrombin as it is formed in plasma. It specifically activates heparin cofactor II (HCII), a plasma protease inhibitor which inhibits thrombin but not other proteases involved in hemostasis. HCII is activated by fractions of 12 or more residues in length that contain an octasaccharide sequence required for binding to the inhibitor.

Suitable dermatan sulfates include those disclosed in Tollefsen, "Heparin and Related Polysaccharides," Lane DA, Björk 1, Lindahl U (Eds), Plenum Press, N.Y., pp 167–76 (1992), Van Gorp, "Heparins and Structurally-Related Glycosaminoglycans," *Clin. Hemost. Rev.* 9:17–8 (1995); and Nadkarni et al., "Preparation and biological activity of N-sulfonated chondroitin and dermatan sulfate derivatives," *Carbohydrate Res.*, 290:87–96 (1996), the contents of which are hereby incorporated by reference.

D. Dermatan Sulfate Derivatives

Native dermatan sulfate (DS) is a better anticoagulant than heparin and is better able to facilitate inhibition of surface-bound thrombin. The specific heparin cofactor II (HCII)-mediated anti-thrombin (IIa) activity of DS has been significantly increased in one dermatan sulfate, Intimatan (CL-03135).

Smith degradation of Intimatan affords a fragment (Intimatan RD) with most of its HCII-mediated anti-IIa activity intact and with aldehyde terminal groups. RD reacts with primary amines to give labile Schiff-bases that can be converted into stable secondary amines by reduction with sodium cyanoborohydride. The anti-IIa activity of Intimatan is less than 60 u/mg, whereas the activity of RD is less than 40 u/mg.

E. Heparan Sulfates

Heparan sulfate, otherwise known as heparitin sulfate or heparin monosulfate, is a generic term describing polysaccharides which are linear and consist of N-acetylated [→4] alpha- D-GlcNpS-(1→4)-ββ-D-GlcAp or alpha-L-ldoAp (1→] that are arranged mainly in a segregated manner. Approximately 25% of the total polymer is initially formed by alternating arrangements of the two disaccharide units, →4)alpha-D-GlcNps(1–>4)UAp (1→4) alpha-D-GlcNpAc (1→4)UAp(1→4)alpha-D-GlcAp(1→. The polymer is formed as a repeating →4)alpha-D-GlcNpAc(1→4)-ββ-D-GlcAp (1→disaccharide sequence that is attached to a serine residue of a core protein through a tetrasaccharide, glucuronosyl →galactosyl →galactosyl →xylosyl, linkage region. It then undergoes partial N-deacetylation followed by N-sulfation of the newly exposed amino groups, partial C-5 epimerization of D-GlcAp to L-IdoAp and O-sulfation. O-sulfates are always found in proximity to N-sulfates which enhances the clustering of the sulfate residues and the heterogeneity in chemical composition and charge density of heparan sulfate. Suitable heparan sulfates are disclosed, for example, in Griffin et al., "Isolation and characterization of heparan sulfate from crude porcine intestinal mucosa peptidoglycan," *Carbohydrate Res.*, 276:183–197 (1995), the contents of which are hereby incorporated by reference.

F. Heparin Derivatives

Deaminative hydrolysis of unfractionated heparin with nitrous acid selectively cleaves the glycosidic bonds of the N-sulfated glucosamine residues with formation of di-, tetra-, hexa and higher saccharides terminated with 2,5-anhydro-D-mannose (AM) residues as reducing terminal groups. The terminal AM residues may be stabilized with sodium borohydride or coupled to an aminated surface by reductive amination.

Periodate causes the cleavage of carbon-carbon bonds if both adjacent carbons bear hydroxyl groups, or a hydroxyl group and an amino group. Unsulfated uronic acid residues in heparin are susceptible to periodate oxidation or Smith degradation. Fragments from periodate-oxidized heparin are larger than those obtained by nitrous acid degradation, reflecting relatively low contents of nonsulfated uronic acids. Those heparins containing aldehyde (CHO) moieties undergo reversible Schiff-base reactions with organic amines, and when treated with sodium cyanoborohydride, the Schiff base intermediate can be reduced to its corresponding amine forming an irreversible bond. In both these instances, the ATIII-binding site remains functionally intact.

Suitable heparin derivatives are described, for example, in Kosakai et al., "Isolation and Characterization of Sulfated Disaccharides from the Deamination Products of Porcine Heparin," *J. Biochem.*, 83:1567–75 (1978); Braswell, "Heparin: Molecular Weight and Degradation Studies," *Biochim. Biophys. Acta*, 158:103–106 (1968); Fransson and Lewis, "Relationship between anticoagulant activity of heparin and susceptibility to periodate oxidation," *FEBS Lett.*, 97: 119–23 (1979); Nagasawa and Inoue, "De-N-sulfation," *Meth. Carbohydrate Chem.*, VIII: 291–4 (1980); and Liu et al., "New Approaches for the Preparation of Hydrophobic Heparin Derivatives," *J. Pharm. Sci.* 83: 1034–1039 (1984), the contents of which are hereby incorporated by reference.

G. Heparin Fractions

Much of the heparin structure can be represented as a repeating trisulfated disaccharide. A pentasaccharide- containing trisulfated glucosamine residues represents the proposed structure of porcine intestinal mucosa heparin that specifically binds to antithrombin III. About a third of the molecules in unfractionated heparins contain this structure. The remaining 70% has no ATIII-dependent anti-clotting activity, but mediates the inhibition of thrombin through heparin cofactor II. The pentasaccharide sequence by itself is structurally incapable of inhibiting thrombin because molecules of at least 18 saccharides are required for simultaneous binding of heparin to ATIII and thrombin. As compared to unfractionated heparin, the fractions have either reduced or increased ATIII-mediated inhibition of thrombin and anti-Factor Xa activity.

Suitable heparin fractions are disclosed, for example, in Choay et al., "Structural studies on a biologically-active hexasaccharide obtained from heparin," *Ann. NY Acad. Sci.*, 370:644 (1981); and Laurent et al., "The molecular weight dependency of the anticoagulant activity of heparin," *Biochem. J.*, 175:691(1978), the contents of which are hereby incorporated by reference.

H. Heparin Fragments

Heparin fragments are the result of enzymatic or chemical cleavage in which (I) heparinase cleaves unfractionated heparin linkages between N-sulfated glucosamine and uronic acid with the formation of oligosaccharides bearing 4,5-unsaturated uronic acid at the non-reducing end; (ii) esters of the iduronic carboxyl groups of heparin are subjected to ββ-elimination at alkaline pH with the formation of 4,5-unsaturated uronic acid at the non-reducing end; (iii) nonsulfated uronic acid residues of heparins are cleaved by oxidation with either nitrous acid or periodate, followed by reduction of the resulting aldehyde(s) with borohydride and hydrolysis under mild acidic conditions, thus producing end groups with the remnant of the nonsulfated uronic acid; (iv) the glycosidic bonds of heparin are cleaved by a radical mechanism using hydrogen peroxide, known as oxidative-reductive depolymerization, resulting in fragments having reducing end groups, and (v) heparin chains are cleaved concomitant with sulfation by the action of a mixture of sulfuric and clorosulfonic acids.

Low-molecular weight heparins (LMWHs) are fragments of conventional porcine-derived heparin. LMWHs were developed to provide more selective inhibition of enzyme function and reduce adverse effects. Heparin fragmentation produces products which maintain activity against factor $X_a$ and release antithrombotic factors, but have significantly less activity against factor $II_a$. As a result, treatment with LMWHs provides antithrombotic effects with less anticoagulant effect, lessening the risk of hemorrhage.

Relative to unfractionated heparin, LMWHs exhibit a reduced ability to prolong thrombin inhibition and an enhanced capacity to inhibit factor Xa, thereby contributing to an improved anti-thrombotic effect. The minimum size for anti-thrombin III (ATIII) binding is a pentasaccharide. However, the pentasaccharide-ATIII complex only inhibits factor Xa and not thrombin as heparin oligosaccharides of <5400 D are without cofactor activity for thrombin. Studies have shown that when comparing the rate of thrombosis development or complications, LMWHs have demonstrated similar efficacy as heparin.

One advantage of using LMWHs is that there is a reduced incidence of hemorrhage and HIT relative to heparin.

There are several LMWH products currently on sale in the United States or being actively investigated. These include Enoxaparin™ (Rhone-Poulenc Rorer), Dalteparin™ (Pharmacia&Upjohn), Ardeparin™ (Wyeth-Ayerst) and Centaxarin® FH. Centaxarin® FH (Ardeparin sodium, ML-009723) is the sodium salt of LMWH obtained by the oxidative-reductive depolymerization of porcine mucosal heparinic acid pursuant to FDA Drug Master File 7952.

Enoxaparin™ is typically administered by subcutaneous injection. The recommended adult dose is 30 to 40 mg given twice daily. Dalteparin™ has a longer elimination half-life than Enoxaparin™, allowing once daily dosing. Like Enoxaparin™, Dalteparin™ is administered subcutaneously. The dose is based on units of anti-$X_a$ activity. The recommended adult dose for Dalteparin™ is 2,500 to 5,000 anti-factor $X_a$ units given once daily. Ardeparin™ is dosed based on patient weight. The recommended adult dose is 50 anti-$X_a$ units/kg administered every 12 hours. Disaccharide analysis qualifies FH as a LMWH with substantial retention of the "internal" heparin structure and without any "modified" residues.

Other suitable heparin fragments include those disclosed in Fareed et al., "AT-III Dependence on the biochemical and pharmacologic actions of a low molecular weight heparin," *Thromb. Haemostas.*, 69:1269 (1993); Schäafer et al., "Anticoagulant and lipasemic profile of a new low molecular weight heparin fragment in man," *Thromb. Haemostas.* 69:2402 (1991); and Malinowski et al., "Comparative pharmacologic studies on a new low molecular weight heparin (ML-009723) and Enoxaparin," *Thromb. Haemostas.*69:1260 (1993), the contents of which are hereby incorporated by reference.

I. Heparin Salts

Heparin salts, usually from porcine intestinal mucosa, are polydisperse in chain length and heterogeneous in degree and type of sulfation. Heparin salts are strongly anionic polyelectrolytes and are effective in functions involving binding and release of micro-ions.

Heparin can form salts with both monovalent cations, such as sodium, and divalent cations, such as calcium. Divalent cations such as calcium bind more strongly to heparin than monovalent counterions.

J. Mixtures of Heparin-Like Substances

Mixtures of heparin-like substances can be used. One example of such a mixture is Danaparoid™ sodium. Danaparoid sodium is an alternative anticoagulant in patients who develop heparin-induced thrombocytopenia (HIT) from heparin therapy. Danaparoid is a low molecular weight heparinoid derived from porcine gut mucosa. Its active components consist of heparan sulfate, dermatan sulfate and chondroitin sulfate. The major difference between Danaparoid and other low molecular weight heparins (LMWH) is that Danaparoid is devoid of heparin or heparin fragments. However, similar to LMWHs, it exerts its antithrombotic effect principally through anti-thrombin III-mediated inhibition of factor Xa and, to a much lesser extent, thrombin. The cross-reactivity of Danaparoid with heparin-induced antibodies is reportedly less than 10%.

K. Targeted Heparin and Heparin-Like Substances

Heparin and heparin-like substances can be targeted to the human thrombus with antibodies, such as the high affinity fibrin antibody DD-3B6/22. Binding multifunctional targeted anticoagulants to the thrombus allows the inhibition of other components of thrombus associated procoagulant activity such as the Factor Xa dependent generation of thrombin and the inhibition of platelet activation. Various monoclonal antibodies (such as DD-3B6/22) have been developed which bind to crosslinked fibrin found in clots in situ, often with relatively high affinity (on the order of $10^{-9}$M or less). (See, for example, *J. Nuc. Med.* 35:195–202 (1994), the contents of which are hereby incorporated by reference.)

L. Other Anti-Coagulants

The anti-coagulants discussed below are not intended to be construed as heparin-like substances, and are not equivalents for heparin or heparin-like substances for purposes of the present invention. However, these can optionally be included in the compositions and used in the methods disclosed herein.

Ancrod is an anticoagulant derived from snake venom. Ancrod does not cross-react with heparin-induced antibodies. However, patients can develop neutralizing anti-ancrod antibodies over time. Ancrod reduces fibrinogen levels, thereby decreasing plasma viscosity. It does not inhibit thrombin, which may limit its use in some HIT patients, particularly those who have disseminated intravascular coagulation (DIC) or septicemia.

Warfarin is another widely used anticoagulant. Warfarin has a relatively slow onset of action, taking up to 5 days for full anticoagulant effect.

Hirudin is the active anticoagulant in the saliva of leeches. Hirudin and its peptide analogues, hirulog and argatroban, are also commonly used as anticoagulants.

Other widely used thrombolytic agents or platelet inhibiting substances include streptokinase, urokinase, tissue plasminogen activator, acetyl salicylic acid, coumadin, coumarin, and dipyridamole.

The above anti-coagulants can also be targeted as discussed above with respect to heparin and heparin-like substances.

II. Adenosine Receptor Agonists

Three major classes of adenosine receptors, classified as $A_1$, $A_2$, and $A_3$, have been characterized pharmacologically. $A_1$ receptors are coupled to the inhibition of adenylate cyclase through $G_i$ proteins and have also been shown to couple to other second messenger systems, including inhibition or stimulation of phosphoinositol turnover and activation of ion channels. $A_2$ receptors are further divided into two subtypes, $A_{2A}$ and $A_{2B}$, at which adenosine agonists activate adenylate cyclase with high and low affinity, respectively. The $A_3$ receptor sequence corresponds to a novel, functional adenosine receptor.

Adenosine binds to all four adenosine receptor sites in a non-specific manner. Adenosine has a relatively short half-life in vivo (less than about 30 seconds), although it is effective at relatively low doses. In one embodiment, adenosine solutions are administered intravenously over an extended period of time to produce the desired effect. Chronic administration of adenosine over a period of a week or more has an angiogenic effect, which is increased by the co-administration of heparin or heparin-like substances.

Agonism at the A2a and A2b receptors is responsible for the angiogenic effect. Adenosine receptor agonists have been developed which have high affinity and selectivity for these receptors. Suitable $A_2$ agonists include 2-[p-(2-carboxyethyl)phenethyl-amino]-5'-N-ethylcarboxamidoadenosine (CGS-21680), a selective adenosine $A_2$-receptor agonist, 4-[2-[[6-Amino-9-(N-ethyl-b-D-ribofuranuronamidosyl)-9H-purin-2-yl]amino]ethyl]benzenepropanoic acid, a selective adenosine $A_2$ receptor agonist, and CV-1808 (Glaxo Wellcome). Other $A_2$ agonists include those described in Niiya et al., *J. Med. Chem.*, 35:4557–4561(1992); Ueeda et al., *J. Med. Chem.*, 34:1340–1344 (1991), Niiya et al., *J. Med. Chem.*, 35:4562–4566 (1992), and Ueeda et al., *J. Med. Chem.*, 34(4):1334–1339 (1991), the contents of which are hereby incorporated by reference.

The use of adenosine $A_1$ and $A_3$ receptor agonists is associated with cardioprotection. Accordingly, the compositions can optionally include $A_1$ and $A_3$ receptor agonists in addition to the adenosine $A_2$ receptor agonists. Suitable $A_1$ agonists include $N^6$-cyclopentyladenosine (CPA), a selective adenosine $A_1$ receptor agonist, 2-chloroadenosine, CPA, R-PIA,GR 79236 (Glaxo Wellcome). Suitable $A_3$ agonists include IB-MECA (1-Deoxy-1-[6-[[(3-iodophenyl)methyl]amino]-9H-purin-9-yl]-N-methyl-β-D-ribofuranuronamide), a selective $A_3$ adenosine receptor agonist, R-PIA ((R)-$N^6$-(phenylisopropyl)adenosine), and NECA (5'-N-ethylcarboxamido adenosine) (Glaxo Wellcome).

Other adenosine receptor agonists include those taught in U.S. Pat. Nos. 3,819,612, 3,819,613, 4,954,504, 5,034,381, 5,063,233, 5,140,015, 5,278,150, and 5,593,875, the contents of each of which are incorporated herein by reference.

Methods of Treatment

The adenosine $A_2$ receptor agonist and heparin and/or heparin-like substance can be used in a method for promoting angiogenesis in a patient in need thereof. The method involves the co-administration of an effective amount of heparin or a heparin-like substance and an effective amount of an adenosine $A_2$ receptor agonist in low, daily dosages for a week or more. The method may be used as a treatment to restore cardiac function after a myocardial infarction. The method may also be used to improve blood flow in patients with coronary artery disease suffering from myocardial ischemia or inadequate blood flow to areas other than the heart, for example, peripheral vascular disease, for example, peripheral arterial occlusive disease, where decreased blood flow is a problem.

The compounds can be administered via any medically acceptable means which is suitable for the compound to be administered, including oral, rectal, topical or parenteral (including subcutaneous, intramuscular and intravenous) administration. For example, adenosine has a very short half-life. For this reason, it is preferably administered intravenously. However, adenosine $A_2$ agonists have been developed which have much longer half-lives, and which can be administered through other means. Heparin and heparin-like substances can be administered, for example, intravenously or by subcutaneous administration.

In some embodiments, the adenosine $A_2$ receptor agonist and heparin or heparin-like substance are administered via different means of administration. For example, the heparin or heparin-like substance can be administered in a once-daily subcutaneous injection, and the adenosine $A_2$ receptor agonist can be administered intravenously for a given period of time.

The amounts of the adenosine $A_2$ receptor agonist and heparin or heparin-like substance required to be effective in stimulating angiogenesis will, of course, vary with the individual being treated and is ultimately at the discretion of the physician. The factors to be considered include the condition of the patient being treated, the efficacy of the particular adenosine $A_2$ receptor agonist being used, the nature of the formulation, and the patient's body weight. Occlusion-treating dosages of heparin or a heparin-like substance and an adenosine $A_2$ receptor agonist are any dosages that provide the desired effect. However, a suitable occlusion-treating dose of heparin (or heparin-like substance) and an adenosine $A_2$ receptor agonist is in the range of about 5000 to about 10,000 U/d heparin and about 40 mg to about 80 mg of an adenosine $A_2$ receptor agonist for ten days. While it possible to administer heparin (or a heparin-like substance) and an adenosine $A_2$ receptor agonist simultaneously, preferably heparin (or a heparin-like substance) is given as a bolus about twenty minutes before starting the administration of the adenosine $A_2$ receptor agonist.

Typically, when heparin is used, it is infused as a bolus of about 15,000 U about 15 minutes prior to the adenosine $A_2$ receptor agonist administration. When adenosine is used as the adenosine $A_2$ receptor agonist, it is then infused for about 5 to about 8 minutes at a rate of about 140 $\mu$g/Kg/min (based on body weight). Thus, a total dose for a 80 Kg patient is about 67 mg. This dosage regiment is repeated daily for about 10 days. The adenosine $A_2$ receptor agonist-heparin infusions can be used to stimulate angiogenesis in patients with symptomatic coronary artery disease in place of other more invasive and expensive therapies such as angioplasty or even coronary artery bypass grafting surgery (CABG).

Effective doses for heparin-like substances and for adenosine $A_2$ receptor agonists other than adenosine are well known to those of skill in the art, and, in some cases, have been described above. Generally, for heparin-like substances, an effective dose is that which maintains the anti-$X_a$ level between 0.5 and 1.0 units/ml. This range has been shown to optimize antithrombotic activity while avoiding adverse effects. Suitable effective dose for adenosine $A_2$ receptor agonists other than adenosine are typically in the range of about 0.1 $\mu$g/kg to about 10 mg/kg body weight per day, preferably in the range of about 1 mg/kg to about 3 mg/kg per day.

The adenosine $A_2$ receptor agonist can be administered to a patient in any pharmacologically and pharmaceutically acceptable form. Preferably, the agonist is administered via a continuous, intravenous infusion, more preferably, in an isotonic, aqueous solution. Both the heparin (and/or the heparin-like substance) and the adenosine $A_2$ receptor agonist can be administered in sterile, buffered, dilute aqueous solutions. Preferably, excipients such as preservatives, stabilizers, and antioxidants are added to these solutions. The prototypical adenosine $A_2$ receptor agonist, adenosine, per se, can be obtained from several sources, e.g., from Fujisawa under the trademark Adenoscan®. Likewise, pharmaceutical forms of heparin and heparin-like substances, such as sodium heparin, are also readily available.

The total daily dose may be given as a single dose, multiple doses, e.g., two to six times per day, or by intravenous infusion for a selected duration. Dosages above or below the range cited above are within the scope of the present invention and may be administered to the individual patient if desired and necessary. For example, for a 75 kg mammal, a dose range for the adenosine $A_2$ receptor agonist would be about 75 mg to about 220 mg per day, and a typical dose would be about 150 mg per day. If discrete multiple doses are indicated, treatment might typically be 50 mg of a compound given 3 times per day. In one embodiment, the adenosine $A_2$ agonist alone causes the beneficial effect, without the need for co-administration of heparin or a heparin-like substance.

Formulations

The compounds described above are preferably administered in a formulation including an adenosine $A_2$ receptor agonist and heparin and/or a heparin-like substance together with an acceptable carrier for the mode of administration. Any formulation or drug delivery system containing the active ingredients, which is suitable for the intended use, as are generally known to those of skill in the art, can be used. Suitable pharmaceutically acceptable carriers for oral, rectal, topical or parenteral (including subcutaneous, intraperitoneal, intramuscular and intravenous) administration are known to those of skill in the art. The carrier must be pharmaceutically acceptable in the sense of being compatible with the other ingredients of the formulation and not deleterious to the recipient thereof.

Formulations suitable for parenteral administration conveniently include sterile aqueous preparation of the active compound which is preferably isotonic with the blood of the recipient. Thus, such formulations may conveniently contain distilled water, 5% dextrose in distilled water or saline. Useful formulations also include concentrated solutions or solids containing the compound of formula (I) which upon dilution with an appropriate solvent give a solution suitable for parental administration above.

For enteral administration, a compound can be incorporated into an inert carrier in discrete units such as capsules, cachets, tablets or lozenges, each containing a predetermined amount of the active compound; as a powder or granules; or a suspension or solution in an aqueous liquid or non-aqueous liquid, e.g., a syrup, an elixir, an emulsion or a draught. Suitable carriers may be starches or sugars and include lubricants, flavorings, binders, and other materials of the same nature.

A tablet may be made by compression or molding, optionally with one or more accessory ingredients. Compressed tablets may be prepared by compressing in a suitable machine the active compound in a free-flowing form, e.g., a powder or granules, optionally mixed with accessory ingredients, e.g., binders, lubricants, inert diluents, surface active or dispersing agents. Molded tablets may be made by molding in a suitable machine, a mixture of the powdered active compound with any suitable carrier.

A syrup or suspension may be made by adding the active compound to a concentrated, aqueous solution of a sugar, e.g., sucrose, to which may also be added any accessory ingredients. Such accessory ingredients may include flavoring, an agent to retard crystallization of the sugar or an agent to increase the solubility of any other ingredient, e.g., as a polyhydric alcohol, for example, glycerol or sorbitol.

Formulations for rectal administration may be presented as a suppository with a conventional carrier, e.g., cocoa butter or Witepsol S55 (trademark of Dynamite Nobel Chemical, Germany), for a suppository base.

Alternatively, the compound may be administered in liposomes or microspheres (or microparticles). Methods for preparing liposomes and microspheres for administration to a patient are well known to those of skill in the art. U.S. Pat. No. 4,789,734, the contents of which are hereby incorporated by reference, describes methods for encapsulating biological materials in liposomes. Essentially, the material is dissolved in an aqueous solution, the appropriate phospholipids and lipids added, along with surfactants if required, and the material dialyzed or sonicated, as necessary. A review of known methods is provided by G. Gregoriadis, Chapter 14, "Liposomes," *Drug Carriers in Biology and Medicine*, pp. 287–341 (Academic Press, 1979).

Microspheres formed of polymers or proteins are well known to those skilled in the art, and can be tailored for passage through the gastrointestinal tract directly into the blood stream. Alternatively, the compound can be incorporated and the microspheres, or composite of microspheres, implanted for slow release over a period of time ranging from days to months. See, for example, U.S. Pat. Nos. 4,906,474, 4,925,673 and 3,625,214, and Jein, TIPS 19:155–157 (1998), the contents of which are hereby incorporated by reference.

In one embodiment, the heparin or heparin-like substance and/or the adenosine $A_2$ agonist can be formulated into a liposome or microparticle which is suitably sized to lodge in capillary beds following intravenous administration. When the liposome or microparticle is lodged in the capillary beds surrounding ischemic tissue, the agents can be administered locally to the site at which they can be most effective. Suitable liposomes for targeting ischemic tissue are generally less than about 200 nanometers and are also typically unilamellar vesicles, as disclosed, for example, in U.S. Pat. No. 5,593,688 to Baldeschweiler, entitled "Liposomal targeting of ischemic tissue," the contents of which are hereby incorporated by reference.

Preferred microparticles are those prepared from biodegradable polymers, such as polyglycolide, polylactide and copolymers thereof. Those of skill in the art can readily determine an appropriate carrier system depending on various factors, including the desired rate of drug release and the desired dosage.

In one embodiment, the formulations are administered via catheter directly to the inside of blood vessels. The administration can occur, for example, through holes in the catheter. In those embodiments wherein the active compounds have a relatively long half life (on the order of 1 day to a week or more), the formulations can be included in biodegradable polymeric hydrogels, such as those disclosed in U.S. Pat. No. 5,410,016 to Hubbell et al. These polymeric hydrogels can be delivered to the inside of a tissue lumen and the active compounds released over time as the polymer degrades. If desirable, the polymeric hydrogels can have microparticles or liposomes which include the active compound dispersed therein, providing another mechanism for the controlled release of the active compounds.

The formulations may conveniently be presented in unit dosage form and may be prepared by any of the methods well known in the art of pharmacy. All methods include the step of bringing the active compound into association with a carrier which constitutes one or more accessory ingredients. In general, the formulations are prepared by uniformly and intimately bringing the active compound into association with a liquid carrier or a finely divided solid carrier and then, if necessary, shaping the product into desired unit dosage form.

The formulations can optionally include additional components, such as various biologically active substances such as growth factors (including TGF-β, basic fibroblast growth factor (bFGF), epithelial growth factor (EGF), transforming growth factors α and β (TGF α and β), nerve growth factor (NGF), platelet-derived growth factor (PDGF), and vascular endothelial growth factor/vascular permeability factor (VEGF/VPF)), antivirals, antibacterials, antiinflammatories, immunosuppressants, analgesics, vascularizing agents, cell adhesion molecules (CAM's), and anticoagulants other than heparin or heparin-like substances.

In addition to the aforementioned ingredients, the formulations may further include one or more optional accessory ingredient(s) utilized in the art of pharmaceutical formulations, e.g., diluents, buffers, flavoring agents, binders, surface active agents, thickeners, lubricants, suspending agents, preservatives (including antioxidants) and the like.

Determination of the Degree of Activity for the Compounds

The activity of the compounds can be readily determined using no more than routine experimentation using any of the following assays.

A. Heparin or Heparin-Like Substances:

The HCII-mediated anti-IIa activity of a heparin-like substance can be determined in a purified system by incubating a sample solution with purified HCII and thrombin. Chromogenic substrate can be added and the amidolytic thrombin activity measured at 405 nm.

B. Adenosine Receptor Agonists

The activity and selectivity of the adenosine receptor agonists for each of the adenosine receptors can be readily determined using no more than routine experimentation using any of the following assays.

Binding Assays.

The prototypical allosteric enhancer PD 81,723, (see Bruns et al., *Mole. Pharm.*, 38:939 (1990), Cao et al., *Gen Pharmac.* 26:1545 (1995), and Amoah-Apraku et al., *J Pharm. Exper. Ther.* 266(2):611(1993)) has both enhancing and inhibitory activity at the $A_1$AdoR. Therefore, the effect of adenosine agonists can be determined on both the agonist [$^3$H]CCPA and the antagonist [$^3$H]CPX binding to membranes prepared from CHO cells stably expressing the human $A_1$ AdoR (CHO-hu$A_1$ AdoR). The enhancing activity can be estimated by the magnitude of the increase in [$^3$H]CCPA binding whereas the inhibitory and (or antagonistic) activity can be evaluated by the potency of the agonists to compete for the specific binding of [$^3$H]CPX. A suitable method for preparing membranes of CHO cells expressing hu$A_1$ AdoR, and the protocols for the radioligand binding assays is described by Kollias-Baker et al., (*JPET*, 281, 761(1997) and *Circ. Res.*, 75, 961 (1994)).

Similar assays for assaying A2 and A3 activity are well known to those of skill in the art.

EXAMPLES

The following examples illustrate aspects of the present invention but should not be construed as limitations. The symbols and convention used in these examples are consistent with those used in contemporary medical and scientific literature.

Example 1

Evaluation of the Effectiveness of the Heparin/Adenosine Compositions

Background

The following open-label placebo-controlled trial was conducted to determine whether the repeated intravenous administration of adenosine and heparin could mimic physiologic angiogenesis and reduce the amount of exercise-induced myocardial ischemia in patients.

Methods

Subjects with chronic stable angina refractory to conventional medical therapy and unsuited for surgical therapy received either adenosine (140 µg/kg/min for 6 minutes) and heparin (10,000 U bolus; n=9) or placebo(n=6), daily for 10 days. All patients underwent baseline and follow-up exercise testing with Thallium 201 SPECT myocardial perfusion imaging. A semiquantitative assessment of the severity of the perfiusion abnormalities was calculated by two blinded investigators.

Findings

Compared to baseline there was no significant change in exercise duration or in the peak rate-pressure product achieved with either placebo or adenosine and heparin. There was, however, a significant reduction in the severity of the myocardial perfusion abnormality seen in patients who received adenosine and heparin compared to placebo.

Interpretation

Repeated administration of adenosine and heparin reduced the amount of exercise-induced ischemia in patients with chronic stable angina refractory to conventional treatment.

Methods

1. Patient Population

Inclusion criteria: Patients were included if they had a history of chronic stable angina pectoris, evidence of myocardial ischemia on exercise as measured by TI-201 SPECT myocardial perfusion imaging performned within the previous 3 months, and were not candidates for coronary revascularization procedures (e.g. CABG or PTCA). In each case, exercise TI-201 SPECT was performed as part of the protocol, with informed consent.

Exclusion criteria: Patients with NYHA class III or IV congestive heart failure, left ventricular ejection fraction less than 20%, coronary revascularization within 3 months (e.g. CABG or PTCA), or who had experienced a cardiac event (e.g. myocardial infarction or unstable an gina) within the prior 3 months were excluded. In addition, patients on anticoagulation therapy that could not be interrupted, patients with a predisposition to hemorrhage, active wheezing, or advanced heart block were also excluded.

2. Protocol Design

This study was an open-label placebo-controlled study to assess the efficacy of repeated infusions of adenosine and heparin. After the screening process, which consisted of clinical evaluation, laboratory studies (Protrombin time (PT), Tissue Tromboplastin time (PTT), and platelets), and exercise TI-201 SPECT, patients received either the protocol infusion (adenosine/heparin) or a control saline infusion. The infusion was administered daily for 10 days and was given in the morning to patients after an overnight fast.

The protocol infusion consisted of heparin, which was administered as an intravenous bolus of 10,000 U, and intravenous adenosine which was infused 15 minutes later for 6 minutes at a rate of 140–µg/kg/min for a total dose of 0.84 mg/kg. Continuous 3-lead ECG monitoring was performed during and for 10 minutes after the infusion. The 12-lead ECG, blood pressure and heart rate were recorded at baseline, at 1-minute intervals during and for 10 minutes after the infusion. Patients were observed for three hours following the administration of either active or placebo treatment.

3. Thallium-201 SPECT Protocol

All patients underwent a symptom-limited exercise test with the Standard Bruce protocol before and within 1 week after completion of treatment.

Exercise duration and nature of the symptomatic endpoint were noted. ST segment changes were noted and their relationship to symptoms and the rate-pressure product (heart rate×systolic blood pressure, beats mm Hg/sec) were assessed in the presence of isoelectric ST segment and normal conduction. In addition, the rate-pressure product were recorded at the onset of ST segment changes and at peak exercise.

Near peak exercise, 3–3.5 mCi of TI-201 was injected. The patients continued to exercise for an additional 30–60 seconds. TI-201 SPECT acquisition was begun 15 minutes after isotope injection and performed again 4 hours later, and after reinjection of an additional 1 mCi of Tl-201 when indicated acquisition of 24 Hs images was performed.

4. SPECT acquisition protocol.

All SPECT studies were done with a dual head Optima camera (General Electric, Milwaukee Mich.), equipped with a low-energy collimator and a Genie computer. A circular 1800 acquisition was performed with 16 projections over 900 for each head at 40s/projection after stress, at 4 hours and after 24 hours when needed. Two energy windows were utilized, a 20% window centered at the 68- to 80-keV and a 10% window centered at 167 keV. Images were acquired using a 64×64 image matrix. All images were evaluated for patient motion and other quality assurance measures including for field non-uniformity and center of rotation. Preprocessing was performed using a Butterworth filter of order 10 with a cutoff frequency of 40% Nyquist. A ramp filter was used to reconstruct the transaxial tomograms in 6 mm slice thickness. Short axis, vertical, and horizontal long axis tomograms of the left ventricle were extracted from the reconstructed transaxial tomogram by performing appropriate transformation with interpolation and displaying according to the standard format.

Image Interpretation

Visual interpretation used short-axis, vertical, and horizontal long axis myocardial tomograms presented on a standard nuclear medicine display using a standard software (Medview, Med Image, Inc, Ann Arbor, Mich.). The intensity of each image set was normalized to the highest pixel value in the myocardium.

A semiquantitative visual interpretation was performed utilizing short-axis, vertical, and horizontal long axis myocardial tomograms on a total of 29 segments. Each segment was scored for regional activity by the consensus of two experienced observers, who were blinded to the patient treatment and imaging sequence, using a 5-point scoring system (0=normal, 1=slightly reduced; 2=moderate reduced; 3=severely reduced, and 4=tracer uptake equal of background).

To evaluate the extent and severity of the perfusion defect, three indices were derived from the score analysis.

To assess the extension of the perfusion defect, the percentage of defect size was obtained, at stress and rest, by dividing the number of segments with an abnormal score by 29 (number of total segments).

To assess the severity of the induced perfusion abnormality, the stress defect percentage was defined as the total stress score divided by the maximum defect score of 116 [product of the total number of segments (29) and the maximum defect score (4)].

The stress image set for each subject was then compared with the corresponding rest image set, and the percentage of ischemic myocardium was calculated as the total stress score minus the rest score divided by 116.

Criteria For Abnormality

A segment with a score >2 was considered to have a defect. A SPECT study was considered abnormal if two or more segments had a stress score of >2. A reversible perfusion defect was defined as one in which a change in the score between stress and rest was more than 1. Nonreversible defects were those with stress scores of 4, 3, or 2 with no change at rest.

Criteria For Improvement After Treatment

This was defined as a decrease in the segmental perfusion score of more than 1. This variation was shown to exceed the level of interobserver variability in prior studies and specifically in relation to the current methodology.

Reproducibility of the Semiquantitative Score Analysis.

Ten myocardial perfusion studies were randomly selected from our database for evaluation. The studies were read independently and scored as noted above by two expert readers. There were 4 normal and 6 abnormal studies. Observers agreed exactly in the score in 266 of 290 segments (92%), and different no more than 1 grade in the remaining 24 of 290 segments (8%). A total of 112 abnormal reversible segments were observed. Observers agreed exactly as to reversibility of abnormality in 94 of 112 segments (84%), and with a difference no more than 1 in 18 of 112 segments (16%) in all ten studies.

Statistical analysis:

All data are expressed as a mean ±standard error. Comparisons were made using the paired Student's t test when assessing the differences between pre and post-study drug administration and the non-paired Student's t test was used when assessing the differences between treatment groups. The chi-square test was used to compare categorical variables. A $\rho$ value of <0.05 was considered statistically significant.

Results:

Patients.

Sixteen patients were studied, of whom 15 were males. Group 1 (n=10) were treated with the active drug. Group 2 (n=6) received placebo. 88% of patients had undergone coronary bypass surgery. All patients were receiving anti ischemic therapy. The mean left ventricular ejection fraction of the group was 55%. There were no significant clinical differences noted between the two groups (Table 1)

Exercise Stress Testing.

All patients underwent a baseline and a follow-up exercise Tl-201 SPECT perfusion study.

Tests were stopped due to fatigue, shortness of breath, or disabling angina. ST changes could not be evaluated due to baseline ST-T and conduction abnormalities. In Group 1, 6 of 10 patients experienced angina in the baseline exercise test. Only these 6 patients had angina in the follow-up exercise test. The rate pressure product at symptoms onset was 20,197±5,202 at baseline, and 18,083±9,642 at follow-up, p=ns. There was also no difference in the peak rate pressure product achieved at baseline, compared with the follow-up exercise test (23,617±3,088 vs 24,588±3350 p=ns). Patients exercised for 6.0±2.2 minutes at baseline vs 6.5±2.5 minutes at follow-up (p=ns).

In group 2, 5 of 6 patients experienced angina at the baseline and follow-up exercise. The remaining patient who did not experience chest pain during the baseline exercise test, noted shortness of breath at the follow-up exercise test. The rate pressure product at the onset of symptoms was 16,537±3,963 at baseline, and 15,937±3,109 at follow-up, p=0. 71. There was no difference in the peak rate pressure product achieved at baseline, compared with the follow-up exercise test (21,539±4,593 vs 19,500±2008, p=ns). Patients exercised for 5.7±1.4 minutes at baseline vs 6.1±1.9 minutes at follow-up, p=ns) (Table 2)

There was also no difference in the peak rate-pressure-products achieved at baseline and after treatment in those patients treated with the active drug (25,500±2,100 vs 24,600±1,200 P=ns) or placebo (21,700±1,700 vs 19,500±800, p=ns) (Table 2).

Thallium-201 SPECT.

In group 1, the percentage Tl-201 defect size at stress was 61.0±13.4, and 53.4±14.2, p=0.015, at baseline and follow-up, respectively. There was a mean improvement of 12% in the percentage of defect size. The stress defect percentage was 40.0±9.7 and 34.6±11.7, p=0.003, at baseline and follow-up, respectively. A 13% improvement was observed. Finally, the percentage of ischemic myocardium was 31.6±8.7 and 24±9.6, p=0.006 calculated at baseline and at follow-up Tl-201. Again, an improvement of 24% in the score index was observed. These changes also far exceeded the bounds of interobserver variability.

In group 2, the percentage Tl-201 defect size at stress was 53.3±10.9 and 56.3±12, p=ns, at baseline and follow-up, respectively. There was not a significant score change. The Tl-201 stress defect percentage was 35.1±9.3 and 35.3±8.02, p=ns, at baseline and follow-up, respectively. Again, no significant score change was found. The percentage of ischemic myocardium was 24.6±9.05 and 27.7±9.99, p=ns calculated at baseline and at follow-up Tl-201. Again, worsening in the severity of the score was observed.

When response to treatment was defined as an improvement in severity score of more than 2 points, 5 of the 10 patients (50%) treated with adenosine and heparin improved, compared with none of the 6 patients treated with placebo. Interestingly, the 3 patients who had the greatest improvement in perfusion score also had a significant improvement in exercise duration. In these 3 patients, the perfusion score improved by 46% (28.6±4.5 vs 15.3±1.15, p=0.0039) and their exercise duration increased by 1.6 minutes (6.48±2.07 vs 8.04±2.24, p=0.005). No patient in the placebo group improved their exercise duration or perfusion score.

Discussion

In the present study, the repeated administration of adenosine and heparin produced a significant improvement in exercise-induced ischemia as assessed by myocardial perfusion imaging. This reduction in ischemia was not secondary to reduced exercise intensity as assessed by either exercise duration or peak rate-pressure product. In fact, those patients who demonstrated the most marked scintigraphic evidence of improvement in ischemia were the patients who experienced the greatest increase in their exercise duration. Interestingly, no increase in exercise duration or in the peak rate-pressure product achieved was observed. These patients with advanced coronary artery disease may have been deconditioned and more limited by this or other factors than by their angina. The image improvement demonstrates a reduced extent of myocardium at risk, yet this need not directly or dramatically improve symptoms or exercise tolerance. Regardless, those patients treated with adenosine and heparin had a significant improvement in their perfusion scans compared to placebo while exercising to the same workload. These finding clearly demonstrated improved perfusion. The mechanism by which this reduction in ischemia occurred is unknown, but is believed to involve the development of coronary collateral vessels.

Conclusion

Repeated administration of both adenosine and heparin for 10 days in patients with chronic stable angina refractory to conventional therapy was associated with a significant reduction in ischemia as assessed by exercise stress testing with perfusion scintigraphy.

Example 2

Injectable Formulation of Adenosine

The active ingredient and buffering agents are dissolved in propylene glycol at about 55° C. The water for injection is then added with stirring and the resulting solution is filtered, filled into an ampule and the ampule is sealed and sterilized by autoclaving.

| Ingredients | Amount |
|---|---|
| Active ingredient (Adenosine) | 3.0 mg |
| Propylene glycol | 0.4 mL |
| Water for injection* | q.s. 1 mL |

*The term "water for injection" means sterile, purified water containing electrolytes such as sodium chloride and buffering agents so that it is compatible to human physiological fluids such as blood.

Example 3

Injectable Formulation of Adenosine and Heparin

The active ingredient and buffering agents are dissolved in propylene glycol at about 55° C. The water for injection is then added with stirring and the resulting solution is filtered, filled into an ampule and the ampule is sealed and sterilized by autoclaving.

| Ingredients | Amount |
|---|---|
| Active ingredient | |
| (Adenosine) | 3 mg |
| (Heparin) | 10,000U |
| Propylene glycol | 0.4 mL |
| Water for injection | q.s. 1 mL |

What is claimed is:

1. A method for treatment of occlusive peripheral vascular disease, coronary disease and disorders associated with these diseases in a patient in need thereof comprising co-administration of adenosine and heparin and/or a heparin-like substance in low, daily dosages for a week or more, wherein the heparin-like substance is selected from the group consisting of chondroitin sulfates, dermatan sulfates, heparan sulfates, low molecular mass heparin fragments, heparin fractions, heparin salts, and mixtures thereof.

2. The method of claim 1 wherein the disease to be treated is associated with occlusion of coronary vessels.

3. The method of claim 1 wherein the treatment involves the promotion of coronary angiogenesis.

4. The method of claim 1 wherein the adenosine is in the dosage range of about 40 mg to about 80 mg and the heparin or heparin-like substance is in the dosage range of about 5,000 U to about 10,000 U co-administered continuously for about six minutes per day for a week or more.

5. The method of claim 1 wherein the heparin or heparin-like substance is administered as a bolus injection prior to administering the adenosine.

6. The method of claim 1 wherein heparin or a heparin-like substance is administered as a bolus injection of about 50,000 to about 100,000 units, about ten to about twenty minutes prior to administering the adenosine by infusion at a rate of about 100 $\mu$g/kg/min to about 200 $\mu$g/kg/min for about 5 to about 10 minutes every day.

7. The method of claim 5 wherein heparin or a heparin-like substance is administered as a bolus injection of about 10,000 U, about fifteen minutes prior to administering the adenosine by infusion at a rate of about 140 mg/kg/min for about six minutes each day for about ten days.

8. The method of claim 1 wherein the heparin, heparin-like substance and/or adenosine are encapsulated or incorporated in a microparticle or liposome.

9. The method of claim 8 wherein the liposome or microparticle has a size less than 200 nm, and the liposom or microparticle is administered intravenously to the patient, permitting the liposome or microparticle to lodge in capillary beds.

10. The method of claim 1 wherein the heparin, heparin-like substance and/or adenosine are administered via catheter.

11. The method of claim 10, wherein the heparin, heparin-like substance and/or adenosine are present in a polymeric system applied to the inside of a blood vessel via the catheter.

12. A pharmaceutical formulation comprising adenosine and heparin and/or a heparin-like substance in a pharmaceutically acceptable carrier, wherein the heparin-like substance is selected from the group consisting of chondroitin sulfates, dermatan sulfates, heparan sulfates, low molecular mass heparin fragments, heparin fractions, heparin salts, and mixtures thereof.

13. The pharmaceutical formulation of claim 12 wherein the concentration of adenosine is about 40 mg to about 80 mg and the concentration of heparin and/or a heparin-like substance is about 5,000 U to about 100,000 U.

14. The pharmaceutical formulation of claim 12 additionally comprising one or more pharmaceutically acceptable excipients.

15. The pharmaceutical formulation of claim 12 wherein the heparin, heparin-like substance and/or adenosine are encapsulated or incorporated in a liposome or microparticle.

16. The pharmaceutical formulation of claim 15, wherein the liposome or microparticle has a size less than 200 nm.

* * * * *